United States Patent [19]
Bursell et al.

[11] Patent Number: 5,993,001
[45] Date of Patent: Nov. 30, 1999

[54] STEREOSCOPIC IMAGING SYSTEM FOR RETINAL EXAMINATION WITH REMOTE EXAMINATION UNIT

[75] Inventors: Sven-Erik Bursell, Newton; Lloyd M. Aiello, Cambridge; William Kelley Gardner, Newton, all of Mass.

[73] Assignee: Joslin Diabetes Center, Inc., Boston, Mass.

[21] Appl. No.: 08/870,939

[22] Filed: Jun. 5, 1997

Related U.S. Application Data

[63] Continuation-in-part of application No. PCT/US95/15996, Dec. 11, 1995, and a continuation-in-part of application No. 08/353,486, Dec. 9, 1994, abandoned.

[51] Int. Cl.$^6$ ................................................. A61B 3/10
[52] U.S. Cl. ............................................ 351/212; 351/247
[58] Field of Search .................................. 351/205, 206, 351/212, 221, 211, 247, 246; 128/745; 348/61, 77, 78

[56] References Cited

U.S. PATENT DOCUMENTS

| | | | |
|---|---|---|---|
| 5,036,390 | 7/1991 | Masunaga | 358/85 |
| 5,049,147 | 9/1991 | Danon | 606/10 |
| 5,054,907 | 10/1991 | Sklar et al. | 351/212 |
| 5,220,360 | 6/1993 | Verdooner et al. | 351/212 |
| 5,233,517 | 8/1993 | Jindra | 364/413.13 |

OTHER PUBLICATIONS

NASA/Center for Public Service Communications (Jul. 1994) *Working Conference on Telemedicine Policy for the NII: An Invitational Consensus Conference*, Aug. 7–9, 1994.

*Primary Examiner*—Hung Xuan Dang
*Attorney, Agent, or Firm*—Fish & Richardson P.C.

[57] ABSTRACT

An image acquisition unit provides true color high resolution digital images of the retina of the eye to a computer network (14, 16, 18) which interfaces with a central record library and displays the images at a remote work station (20A and 20B) for diagnostic examination. The computer network (14, 16, 18) is also interfaced with a unit for entering medical history information, and the diagnostic data, stereo images and medical records are linked in a relational database allowing all text and image records of the patient to reside on a work station/display (20A and 20B) for review or consultation. A telecommunications link (22) interconnects the computer network and image examination stations with the image acquisition station where the patient is actually examined, so that stereo fundus images may be made available through the computer without degradation for viewing on the examination displays remotely from the room, building, or city where the images are acquired from the patient. By introducing digital true-color normalization at the image acquisition source (34,32), applicant avoids the problem of spurious color artifacts arising when the images are viewed subsequently, or on other monitors.

24 Claims, 3 Drawing Sheets

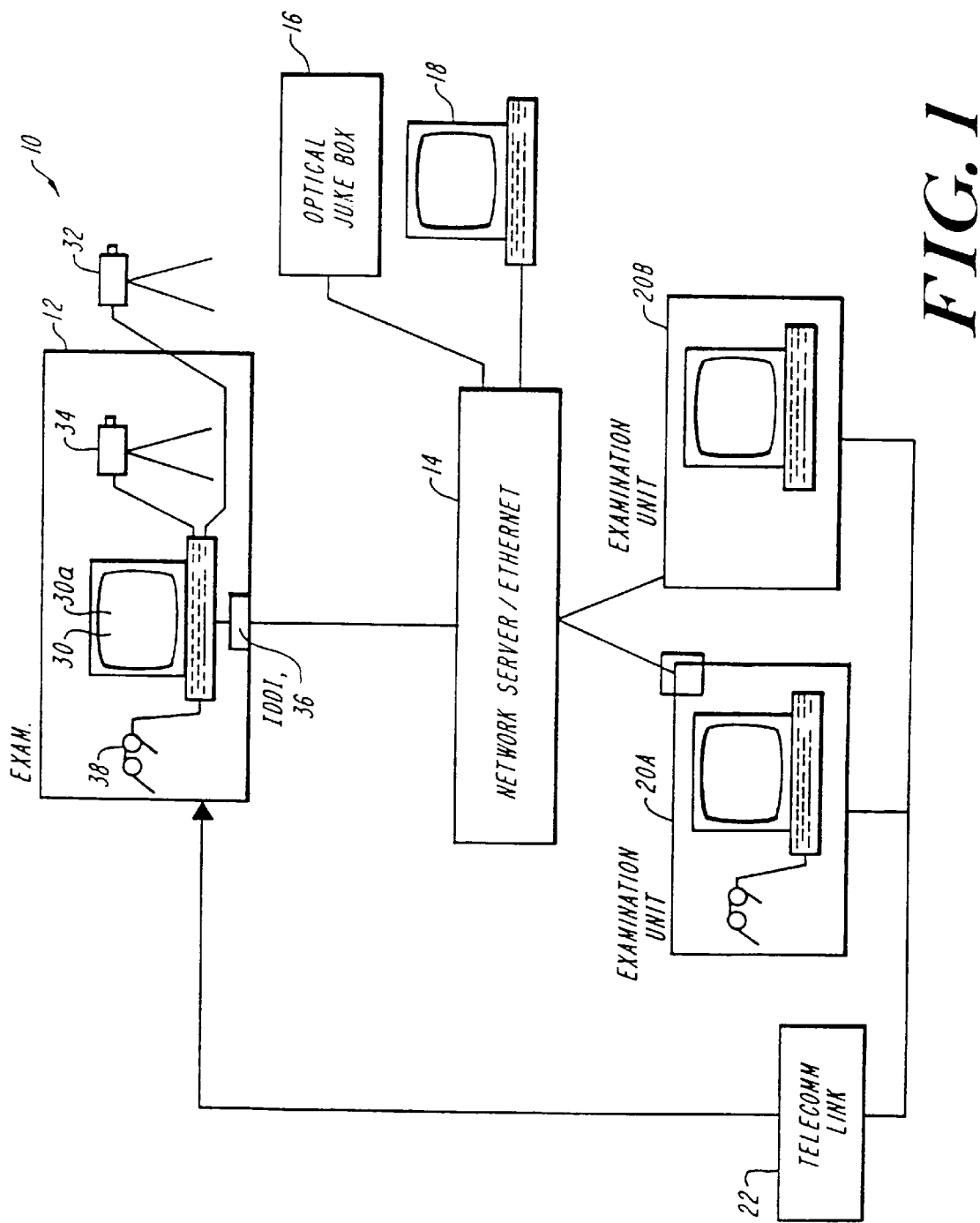

MONITOR SCREEN

| FIELD 4 LEFT IMAGE OF STEREO PAIR | FIELD 4 RIGHT IMAGE OF STEREO PAIR | FIELD 6 LEFT IMAGE OF STEREO PAIR | FIELD 6 RIGHT IMAGE OF STEREO PAIR |
|---|---|---|---|
| FIELD 2 LEFT IMAGE OF STEREO PAIR | FIELD 2 RIGHT IMAGE OF STEREO PAIR | FIELD 1 LEFT IMAGE OF STEREO PAIR | FIELD 1 RIGHT IMAGE OF STEREO PAIR |
| FIELD 3 LEFT IMAGE OF STEREO PAIR | FIELD 3 RIGHT IMAGE OF STEREO PAIR |  | EXTERNAL |
| FIELD 5 LEFT IMAGE OF STEREO PAIR | FIELD 5 RIGHT IMAGE OF STEREO PAIR | FIELD 7 LEFT IMAGE OF STEREO PAIR | FIELD 7 RIGHT IMAGE OF STEREO PAIR |

LAYOUT OF THUMBNAIL STEREO PAIR IMAGE ARRAY
(LEFT AND RIGHT EYES SAME)

*FIG. 2B*

STEREOSCOPIC IMAGING SYSTEM FOR RETINAL EXAMINATION WITH REMOTE EXAMINATION UNIT

This patent application is a continuation-in-part of international application PCT/US95/15996, filed Dec. 11, 1995, which is continuation in part of U.S. patent application Ser. No. 08/353,486, filed Dec. 9, 1994, now abandoned.

FIELD OF THE INVENTION

The present invention relates to systems and methods for examining and treating the retina of an eye, and more particularly, to imaging systems and communication systems that provide stereoscopic images of the retina of an eye.

BACKGROUND OF THE INVENTION

Diabetes is the leading cause of blindness in working age adults. It is a disease that, among its many symptoms, includes a progressive impairment of the peripheral vascular system. These changes in the vasculature of the retina cause progressive vision impairment and eventually complete loss of sight. The tragedy of diabetic retinopathy is that in the vast majority of cases, blindness is preventable by early diagnosis and treatment, but screening programs that could provide early detection are not widespread.

Promising techniques for early detection of diabetic retinopathy presently exist. Researchers have found that retinopathy is preceded by visibly detectable changes in blood flow through the retina. Diagnostic techniques now exist that grade and classify diabetic retinopathy, and together with a series of retinal images taken at different times, these provide a methodology for the early detection of degeneration. Various medical, surgical and dietary interventions may then prevent the disease from progressing to blindness.

In the United States, a 22-hospital collaborative clinical trial, the Early Treatment Diabetic Retinopathy Study (ETDRS) has shown that high risk cases can be identified early, and early treatment can substantially reduce the risk of severe visual loss. Comparative economic studies have estimated that if all diabetic persons received routine annual eye examinations with appropriate intervention, cost savings of hundreds of millions of dollars and avoidance of hundreds of thousands of person-years of blindness would be achieved. The health system performance measures of HEDIS recommend that health maintenance organizations require annual retinal examinations for all diabetic patients.

Despite the existing techniques for preventing diabetic blindness, only a small fraction of the afflicted population receives timely and proper care, and significant barriers separate most patients from state-of-the art diabetes eye care. There are a limited number of ophthalmologists trained to evaluate retinopathy, and most are located in population centers. Many patients cannot afford the costs or the time for travel to a specialist. Additionally, cultural and language barriers often prevent elderly, rural and ethnic minority patients from seeking proper care. Moreover, because diabetes is a persistent disease and diabetic retinopathy is a degenerative disease, an afflicted patient requires lifelong disease management, including periodic examinations to monitor and record the condition of the retina, and sustained attention on the part of the patient to medical or behavioral guidelines. Such a sustained level of personal responsibility requires a high degree of motivation, and lifelong disease management can be a significant lifestyle burden. These factors increase the likelihood that the patient will, at least at some point, fail to receive proper disease management, often with catastrophic consequences.

Accordingly, it would be desirable to implement more widespread screening for retinal degeneration or pathology, and to positively address the financial, social and cultural barriers to implementation of such screening. It would also be desirable to improve the efficiency and quality of retinal evaluation.

SUMMARY OF THE INVENTION

These and other desirable ends are achieved in a system according to the present invention wherein an image collection or acquisition unit provides digitized high resolution true color images of the retina of the eye and a computer network receives and manages these images causing them to be displayed as visual images on a display/monitor workstation for diagnostic examination. Preferably the images are stereo images. The computer network is interfaced with a medical record database or means for entering medical history information, such that the retinal images and medical records are linked in a relational database and accessed together. A telecommunications link interconnects the computer network to the image acquisition station where the patient is actually examined, with a bandwidth such that fundus images are made available through the computer without degradation for viewing on the examination displays remotely from the room, building, or city where the images are acquired from the patient. The images may be taken and viewed stereoscopically for analysis by a trained ophthalmologist or by other trained personnel. A graphic interface operating in conjunction with special processing modules identifies image features, or changes, of diagnostic significance and allows the viewer to enter textual data in the record. The telecommunications system preferably includes a fiber optic link for the image data, and may connect to teleconferencing equipment at either end, allowing an optometrist or trained technician in one location to take and transmit stereo fundus images while consulting in real time with a specialist who analyzes those images at another location.

In a preferred embodiment, the image acquisition station includes a relatively simple apparatus in which a relatively unskilled operator may aim, adjust and actuate the camera to produce true color images, while the examination station includes operator control units for retrieving, displaying and manipulating the images acquired from the image acquisition station. These controls may include image processing modules implemented in software for enhancing feature definition, selectively filtering colors from the image, or implementing block transforms other imaging processes to accentuate the appearance of vessels or surrounding tissue appearing in the stereo image, or identifying changes since a previous imaging session. The image examination stations may receive or retrieve images and display them in spatial order as standard fields, may project a series of standardized images such as the fundus grading slides available from the Fundus Photograph Reading Center of the University of Wisconsin (P.O. Box 5240, Madison Wis., U.S.A. 53705), and may project comparative sets of stereo images for clinical review, feature enumeration and data entry, or other analytic or recording purposes.

The image control or manipulation units may also include control units which operate in real time for sending direct image control signals to the image acquisition station to adjust the level of image resolution, the illumination color or intensity, or the field of view or image orientation. In addition, the telecommunications link advantageously includes an audio channel, to be used for simple verbal consultation and instruction, such as instructing the person operating the imaging camera to aim the camera at a specific site or lesion or make other adjustments or observations. The audio channel may also be used for remote consultations with the evaluating doctor. The image acquisition unit includes high definition digital frame true color imaging equipment, such as a camera or pair of video cameras attached to an ophthalmic imaging device, or a multiplexed single camera aimed at the focal planes of a stereo fundus camera ophthalmic imaging assembly, to generate high definition video frame data, preferably at a sufficient speed to provide time resolution motion pictures or high resolution views of the retinal field. The video image acquisition unit also includes an adjacent or proximal control unit which may include means for inserting alphanumeric information display legends within the video frames to provide information such as patient name, medical record number, date of image and precise time information. In other embodiments, the local control unit may also provide time information and synchronization with a dye injector or other stimulus so that the time marked on each frame reflects the time interval elapsed since the start of a fluorescein or dye angiography, or other procedure. For such a time-evolution procedure, the stereo video frames do not just show the retinal tissue and vasculature, but rather, successive frames provide an evolving image which quantitatively shows both the circulatory capacity and the flow velocity in each vessel or region of the retina. This, together with the elapsed time indication provides a quantifiable record of retinal circulation.

The image acquisition unit preferably includes an adjustment for color matching an image frame before the frame is recorded, allowing all frames of a set, whether recorded at the same or different sessions, to achieve optimal feature visibility and avoid heterochromic artifacts that might otherwise arise when comparing or processing multiple views. The image frames are preferably coded and stored to identify their relative position on the fundus, and the image examination stations selectively display the acquired images as multi-image sets arrayed in accordance with their fundus position, or display images as one or more sets of stereo pairs, or as isomorphic enlargements of a region designated by the operator.

In a preferred embodiment, a fiber optic link interconnects at least a portion of the image acquisition or storage with the computer network, and true color digital images may be taken and displayed in real time to effectively place the specialist-ophthalmologist in immediate control of the diagnostic procedure. In related embodiments, treatment instruments may also be set up at the image acquisition station and continuously monitored or controlled from the examination/display room. Such units may include laser surgery or coagulation units for performing retinal microsurgery. In this case, the operator control units may include means for controlling the power level and aiming of such treatment instrument remotely from the examination room. When operated in this mode, preferably rather than aiming and firing the coagulation unit directly, the control system includes an image analysis module, which allows the ophthalmologist to select the tissue sites on the stereo image video frames displayed in the examination room which are to be treated in the remote station. Once the retinal site coordinates on the image frame are identified, this information is transmitted over the network to the image acquisition application site. The laser coagulation unit at the patient site preferably includes image analysis and target tracking software which allows the identified coordinates on the frame viewed by the ophthalmologist to be located in the current frame scan of the patient's eye, and control interface software to aim the laser unit accordingly. Thus, intervening movement of the patient's eye or destabilization of the instrument aiming system during the time elapsed with transmission and display is corrected by correlating successive frames of the video image to identify the precise physical spot in the current frame at which treatment is to occur.

BRIEF DESCRIPTION OF THE DRAWINGS

These and other features of the invention will be understood from the description below taken together with illustrative figures, wherein:

FIG. 1 illustrates a system constructed according to the present invention for retinal evaluation; and FIG. 2A and 2B illustrate standard fields and a thumbnail array of displayed images.

DETAILED DESCRIPTION OF THE ILLUSTRATED EMBODIMENT

Figure 2A:
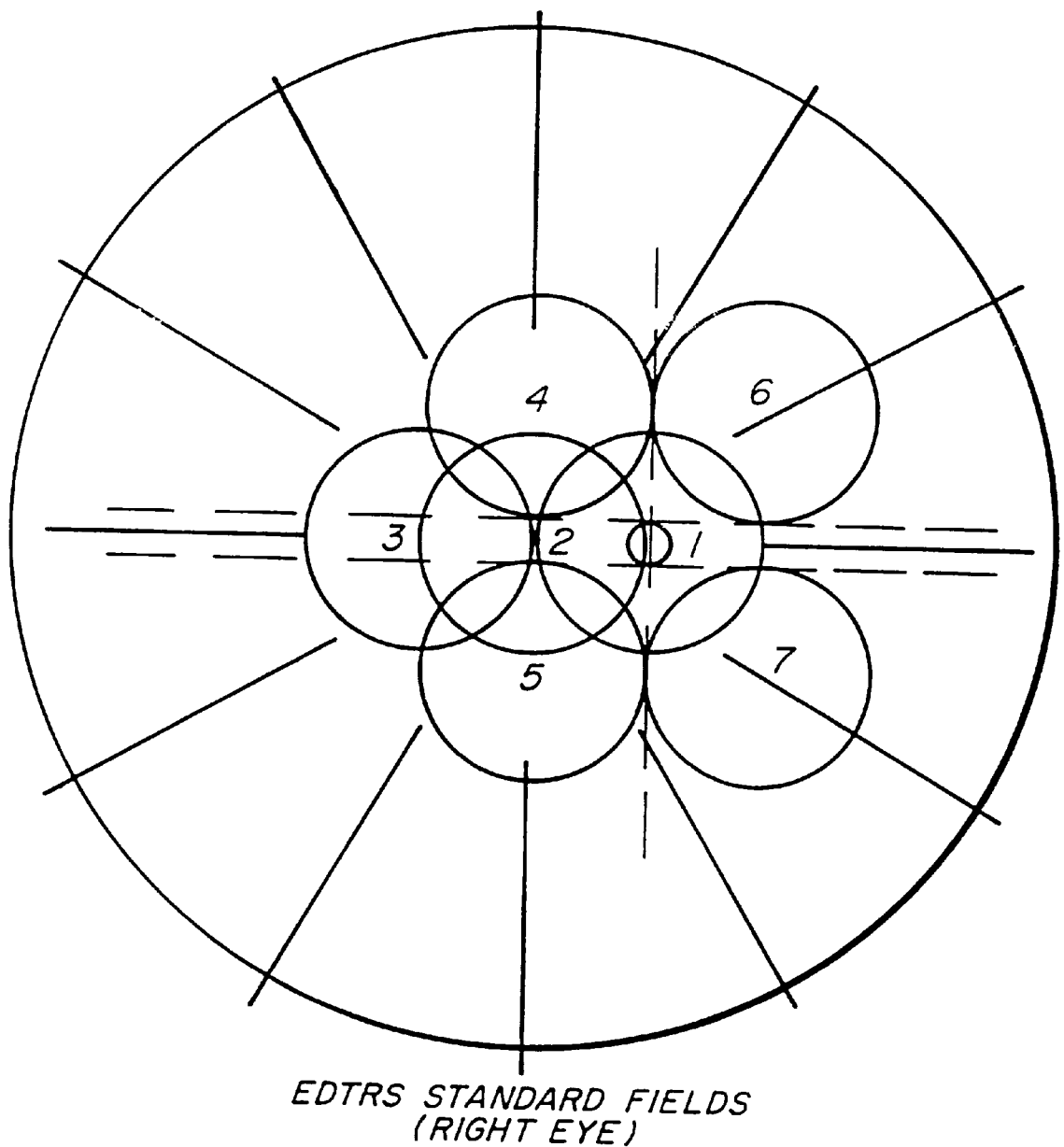

FIG. 1 illustrates a system 10 constructed according to the present invention, for acquiring and examining images of the retina of an eye. As illustrated in FIG. 1, the system 10 includes a data collection unit 12, a network unit 14, a data storage unit 16, a central computer 18, remote work station units 20A and 20B, and a telecommunication link 22. As illustrated in FIG. 1, the network 14 interconnects the other elements of this system 10 so that each element is in communication with each other element. In this way, the system 10 is adapted for communicating information and command signals between one image acquisition station and another image examining station. As such, the system provides an apparatus that allows an operator at a remote work station unit 20 to acquire images and examine the images of a patient located proximal to the data collection unit 12.

In many respects, a basic embodiment of the system of the present invention may be assembled from readily available computing, image conditioning and processing components interfaced with available ophthalmoscopic instruments. A suitable set of network and computer elements to implement the system is described in a system description below, and preferably includes special dedicated cards for graphic acceleration, e.g., image handling and transmission, although the basic image acquisition workstation may operate with relatively simple optical and computer hardware.

Returning to FIG. 1, the data collection or image acquisition unit 12 illustrated in system 10 includes a set of hardware equipment for acquiring high resolution full color retinal images, including a computer processing system 30, a first camera 32 and a second camera 34, a network interface 36 and a set of optional stereo viewing goggles 38. The two video cameras 32, 34 are directed at the focal planes of a stereo fundus camera imaging assembly (not shown), so that they generate views from two different angles, across a triangulation base, of a commonly viewed region of the patient's eye. As discussed further below, this allows photometric analysis of fundus tissue, which in conjunction with special applications processing, is partially or completely automated and integrated with the relational database information of system 10. It will be understood that with suitable optical multiplexing arrangements a single camera, rather than two cameras, may be directed to alternately image each of the two focal planes of the ophthalmic instrument, or that, as is commonly done for photographic image recording, a single fundus camera may be manually shifted by the operator to successively take two different images of the retina which form a stereo pair. In that case, a single camera and no special switching are used. However, in general, the use of two separate video cameras with a stereo fundus camera is preferred so as not to reduce the total amount of light available for forming each image frame and to form uniform and well aligned stereo images at a single instant in time. It will be further understood that the video camera 32 or 34 may be a CCD array or other special two-dimensional sensing device, and need not be a complete "camera" in the consumer product sense. However, by way of example, the presently preferred embodiment may be a commercially available camera of suitable resolution which produces an output video signal in NTSC, PAL or SECAM format. A direct digital camera may also be used, that is, one having a formatted digital output, although in general special drivers will be required to interface such a camera with computer-manageable video frame handling circuitry.

In the illustrated embodiment, the data collection unit 12 is adapted for acquiring stereo images of the fundus of the patient's eye. In a representative embodiment, the camera elements 32 and 34 interface to the two stereo image planes of a Donaldson stereo fundus camera (not shown), and camera elements 32 and 34 are video camera elements of the type suitable for generating high resolution image signals representative of a visual image encoded in a video format such as the NTSC, S-video or other format; each camera element 32 and 34 connects to the computer processing unit 30. The computer processing unit 30 includes a video interface board that is adapted to interface with the camera elements 32 and 34 to receive video signals therefrom along transmission paths such as impedance matched coaxial cables. The video interface cards of the computer unit 30 contain special high speed circuitry for digitizing the video signals and converting them into high resolution, e.g., 1280× 1024 pixel, video frames. This corresponds to an effective resolution of ten to twenty micrometers, with typical fundus camera objective optics. The computer unit 30 also has a provision for processing the captured stereo image frames to generate or allow generation of three dimensional images that can be manipulated and viewed, as will be explained in greater detail hereinafter, by an operator at the data collection unit 12, or at the remote work stations 20A and 20B.

At the image acquisition site, the processor system 30 preferably has a foot switch activation signal for initiating image acquisition, with the camera signals fed to an audio/video processing board such as the J300 board of Digital Equipment Corporation. This circuit performs any necessary video scaling, filtering and color dithering of the video signals received in a standard format from the camera, and produces a normalized output in NTSC or PAL video, or in composite or S-video formats, that is suitable for digital processing. The output of the J3000 board is fed to a twenty-four plane double-buffered graphics accelerator circuit, which digitizes and formats the frames, and provides efficient internal handling and processing in real time for true color high resolution video frames. The accelerator card allows left- and right-video frames to be alternately displayed on the display at twice the normal 70 Hz refresh rate, for stereo viewing. Frame-to-frame spatial correlation then allows a three-dimensional stereo imaging and display program to build and manipulate three-dimensional views of the imaged field of varying appearance, and to form fractal maps of the displayed retinal image topography.

In the illustrated embodiment, the interface element 36 is a separate element connected via a transmission path to the computer 30, and connects the computer unit 30 to the network 14 for transmitting information signals and command signals therebetween. The interface element 36 can be a standard ethernet network card that is adapted for interfacing the computer unit 30 to a standard ethernet network such as the Novell network system, and preferably includes high bandwidth optical fiber data ports and adapters.

As further illustrated in FIG. 1, the display at the data collection unit 12 advantageously operates with a set of stereo goggles. In this embodiment of the present invention the data collection unit 12 is adapted for acquiring and viewing stereo images that represent the fundus of a patients eye and presenting them in an alternating time-sequential fashion on display that enhances the viewer's perception of depth and shading. The computer monitor element 30A works in concert with the stereo goggles 38 to allow an operator to view three dimensional images of the patient's retina. In one embodiment of the present invention, the monitor element 30A is a high resolution video monitor that operates at a frame rate of 140 Hz for displaying a sequence of retinal images taken by the cameras. Each of the frames is captured and indexed, and recorded in temporary storage, such as local disc storage, and the sequence of frames is sent on the network where a massive memory device such as a 700 Gbyte storage unit stores the images as a patient image record. This storage unit can store the records of hundreds or thousands of patients with their fundus images, and may be periodically backed up so that complete records are available for all current patients.

At the monitor, the frame sequence, which may be stopped, if desired, to allow individual frames to be viewed, is viewed through the stereo goggles 38 which act as a time-switched pair of shutters over the operator's eyes. Such stereo goggles 38 can be of the type manufactured by and commercially available from the Stereographics Corporation and used for image display and analysis, in fields such as stereographic survey image analysis. Each viewing lens of the goggles is formed of an electroactive material which is opaque when energized, and when not energized is clear. An IR receiver on the goggles synchronizes the actuation of the left and right lenses with the display of right and left views on the display, so that each eye is blanked during the time the other side view is displayed on the monitor. Since the two stereo frames alternate at a high frame rate, the effect is to form a sequence of stereo video images at the normal 70 Hz refresh rate of the display which appears continuous to the viewer.

The illustrated network system 14 is adapted for carrying video frame information signals and other data or command signals between the image acquisition site and a remote image examination site. In particular, the network element 14 is adapted for carrying high volume information signals representative of many digital stereoscopic images and the various computers or processors are also interfaced with a medical records management program to store the images in a relational database, and make the medical record information available at the examination stations. In a preferred embodiment of the invention, the network includes an optical fiber cable system, and implements an ethernet network protocol. However, the present invention can also be practiced with another suitable network system or configuration that has sufficient bandwidth to carry the information signals representative of the stereoscopic images. Thus, for example, a multichannel direct microwave communications link may be effective to connect the image acquisition unit to a central computer system located within a few miles crosstown, while intra-building optical fiber channels may interconnect medical records and the examination stations within a single building or complex. Leased channel space on a fiber optic link may interconnect acquisition units 12 in distant cities or remote neighborhoods, and satellite up-and-down links may also be used effectively. Furthermore, where sufficient channel space is not readily available, the invention may be practiced in various forms utilizing low frame rates, or at full resolution but with motion studies delayed somewhat to allow transmission and storage of a frame sequence before viewing.

Continuing now with the description of FIG. 1, the network 14 includes basic server software and circuitry for interfacing the central computer system 18 and data storage element 16 with a plurality of work station/display units 20a, 20b, etc., of which two are shown. The data storage element 16 is preferably an optical storage element with associated server circuitry, commonly referred to as an optical jukebox, having a large capacity in the range of seven hundred gigabytes. Incoming image frames from the image acquisition site are placed in storage and also made available over the network directly to an examination unit 20, during the course of a procedure, as discussed further below.

In broad terms, image acquisition is carried out at a first site such as a mobile screening unit or small clinic, or in a medical center in a community which may be remote from the primary hospital housing the units 20a, 20b and computer 18, using equipment as described above in relation to image acquisition unit 12. The context of the examination may involve a local optometrist or ophthalmologist responsible for the patient, and who actually sets up or controls the fundus camera or other ophthalmic instrumentation in the acquisition room. The network connection by satellite, leased line, fiber optic or other communications link provides the video frame and other audio and digital data to the network which, in general, with the other units described below is located at a central research center or ophthalmology department of a teaching hospital. The network and server with a plurality of image examination stations thus form the hub for a number of image acquisition units 12.

Each examination unit 20 may be a relatively powerful work station, with memory for storing and immediately accessing 50–200 Mbytes of data and processing capability including a video accelerator for displaying high resolution true color images. The unit 20 includes a high definition video display, preferably as noted above, a stereo imaging display with specialized viewing discrimination equipment such as infrared-synchronized stereo viewing goggles, and preferably also a digitizing medical records pad and/or keyboard entry system on which a specialist ophthalmologist or specially trained technician viewing the frame can write observations and conclusions of diagnostic relevance. Such a hand-held pad is of the type commonly used by the physician to create standardized medical examination records, and for this application is configured to interface directly to the workstation and software which accommodates the image data in a relational database for accessing and displaying from the existing records in the central data storage, or filling in relevant medical history and other data. A suitable physician's data entry pad is that sold by the Datamedic Corporation, which facilitates entry of medical data and its linking and correlation with data displayed on the screen at the time.

In general, it is contemplated that the examination units 20a, 20b may be located at a "hub" which services a number of image acquisition sites 12. The sites 12 may be simply clinic examination rooms located in the same hospital, but also, due to the unique system architecture, may consist of plural widely separated clinics at different remote sites. The work performed at examination units 20a, 20b may involve the meticulous view of images and tabulation of diagnostic details, such as counting the number of microaneurisms, leaks, scars or the like in particular retinal image fields, or deriving other quantitative measures, as described, for example in the ETDRS Reports Nos. 10–13 at pages 786–834 of Volume 98, Ophthalmology (May 1991 Supplement). It may also involve other less quantitative or less time consuming clinical judgments, as well as various forms of image manipulation, color enhancement, and record annotation. Much of this work can be performed by specially trained technicians, so the organization of an examination center "hub" in this manner will allow the limited number of trained ophthalmologists to examine and treat a vastly greater number of diabetic patients. Typically, twenty or more, and up to five hundred work stations 20 may be located at the hub.

In general, the precise form of imaging effected at acquisition sites 12 will vary depending on the nature of acquisition equipment available at each site 12 (e.g., ophthalmoscope, fundus camera, stereo fundus camera) and the nature of the image capture at that site. In particular, a video camera with subsequent digital frame conversion will produce a true color image frame images with a 6–700 line field resolution which is capable of transmission as under a megabyte of data, whereas a high resolution direct digital camera such as a Kodak DCS 420 or DCS 460 with a 1500×1250 pixel frame will require 2–4 megabytes of information. For diagnostic utility, applicant has found it necessary to use true color images, and to transmit using only image compression protocols that are not glossy. Thus, the availability of a high bandwidth communications channel such as a satellite or fiber optic link is critical to real time consultations, although if only a lesser bandwidth is available it is still possible to transmit images (albeit over several minutes) and undertake remote consultations using the system. By using the DEI-470 color video camera manufactured by Optronics Engineering, or that company's higher resolution DEI-750 3-chip RGB camera, the retina may be imaged in true color using light levels comparable to or less than those employed in the viewing system of a typical retinal fundus camera or ophthalmoscope, and with a resolution of 10–20 micrometers. These cameras, operating with low illumination levels rather than flash and produce images in true color, i.e., visually indistinguishable from that seen through an ophthalmoscope are operated to produce the large number of frames (28) required for diagnostic fundus grading without the drawbacks of existing (flash) fundus photography.

In a presently preferred embodiment for retinal imaging and evaluation, the camera 32 and image acquisition and control unit 12 are configured to produce "normalized" or "absolute" true color images, further enhancing their utility. This is achieved as follows.

One suitable retinal imaging assembly is a fundus camera such as a Nikon NF-505 or Topcon TRC-50 fundus camera assembly which has its customary flash, film transport and supporting electronics removed, and replaced by an Optronics video imaging camera mounted to electronically convert the focused fundus image. As in the system of FIG. 1, an image acquisition processor receives the electronic image data and attends to any necessary signal conversion, formatting, framing or other processing for display or transmission of the electronic images. Furthermore, in this embodiment, a full color LCD display is mounted in a gimbaled setting to the side of the camera where it may be directly viewed by the operator as the camera is aimed at the fundus. As in the embodiment of FIG. 1, the electronic imaging assembly may be a direct digital imaging camera, in which all or a portion of the image signal processing and framing circuitry is incorporated in the camera itself, or may be an analog (video) output imaging tube or array in which the output video signal is subsequently digitized by processor 12 and associated electronics. In any case, the frames imaged by the electronic imaging assembly are also delivered to and displayed on the pivoting LCD color screen, thus allowing a direct and large-scale view of the digital color image being captured by the camera.

In general, it will be understood that retinal images, due to the intrinsic color of background tissue, are of a generally orange-red hue. Moreover, the electronic imaging assembly attached to the fundus camera is intended to function with a relatively low level of continuous illumination rather than flash illumination, and its images may quickly become washed out as illumination increases, or may become a dark brownish purple as the illumination level decreases to a point near the imaging threshold. These light response characteristics stem from the saturation properties of the image sensing CCD portion of the camera, which preferably has an imaging sensitivity below about 0.01–0.2 lux, as well as from the spectral responses of the three different color pixel sets or their filters. Applicant has found that this level of variability, even when the light source is initially set so that the observed tissue appears normal, impairs the diagnostic value of acquired images. This is especially true when the acquired image is to be compared to one or more baseline images acquired at different times, or is one of a set of adjacent or overlapping standardized fields such as used for Airlie House classification of retinopathy. For such images, unintended variations in color, contrast or density may seriously impair the visibility of details, or may prevent meaningful comparisons or determination of changes.

This shortcoming is addressed in accordance with a further aspect of the invention by providing an adjustable illumination source, and normalizing the captured image to the actual appearance of the observed tissue as the images are acquired.

The adjustable illumination source may be, for example, a tungsten linear filament lamp of up to about ten or fifteen watts power. The adjustable source has a spectral output with peaks in the yellow/red region of the spectrum, and the peaks shift from red toward shorter wavelengths as the lamp drive voltage is increased. Variation in this spectral response therefore allows the operator to vary the visual appearance of retinal tissue as the camera is focused on the fundus, and results in a generally greater variation in the color or hue of the displayed images being captured by the camera.

To normalize the captured digital images, the image processor 12 operates in an adjustment mode by providing an image of the current camera image "S" to the LCD display, which is arranged so the operator may simultaneously view the LCD display while looking through the viewing port of the camera assembly. The two images are visually compared by the operator as lamp drive voltage is adjusted, so that the displayed video image ranges through a range of brightness, contrast and relative hues, while the actual observed tissue may appear generally brighter and yellower. The operator then adjusts the lamp until the two images-the LCD display and the direct visual appearance-match as closely as possible in color and intensity in the major (e.g., background tissue) regions of the image. Once the normalized color is adjusted in this manner, the operator clicks on the shutter control switch (e.g., a mouse) and the electronic image frame is stored. This color-matching operation can be performed with accuracy by the human eye, and results in the acquisition of images the digital representations of which are color-matched, despite the actual color balance adjustments of the monitor upon which the operator is observing the images and the camera's spectral response. This color normalization requires that the color balance "transformation" introduced by the monitor in transforming electronic-to-light images be approximately the inverse of the color transformation introduced by the camera in transforming light-to-electronic image signals. While in general the different color transformations over the entire visible spectrum, of the camera and the display, may not be amenable to such a compensating inverse relationship, applicant has found that within the color range encompassed by retinal images, this is dependably achieved by adjusting the camera and display color settings to be approximately inverse under standard light conditions. The necessary recognized settings are generally different from the standard factory-defined default settings for both the video camera and the monitor, but result in a display that approximates the actual clinical appearance of tissue. The operator then needs only to compare the color of the digitized retinal image on the monitor screen to that directly observed through the fundus camera eyepiece, and make minor adjustments to the intensity level of the fundus camera viewing light, in order for the color content of the digitized retinal image on the monitor screen to be the same as that observed directly through the fundus camera eyepiece. The institution of this adjustment protocol for the correct color of the retinal image means that it is no longer necessary to rigorously calibrate both monitor and video camera for every patient. In fact, applicant has found that this procedure for obtaining the correct color for the retinal image functions equally well regardless of the pigmentation of the fundus, i.e., regardless of whether the patient is Caucasian, Asian, African or Hispanic, or otherwise has a specially pigmented retinal background tissue.

By introducing this digital true-color normalization at the image acquisition source, applicant avoids the problem of spurious color artifacts arising when the images are viewed subsequently or on other monitors, e.g., remotely. When images are taken as stereo pairs, each frame of the pair may be normalized as described above.

As described above, the image acquisition system can be operated by personnel with minimal training, primarily that associated with recognition of the different areas of the retina that are needed for diagnosis of the level of diabetic retinopathy, (i.e. the "standard fields") and some practice in obtaining stereo pair images of the same retinal field, as well as basic clerical skills, e.g., familiarity with entering patient demographic data in the appropriate fields of a pen pad medical record entry system. Thus, the operator need not be skilled in the art of taking retinal photographic images. Because the acquisition is video-based, the acquisition of images and the quality of the images is as simple as operating a commercial home use video camera.

As noted above, the invention when practiced with the described Optronics cameras allows accurate image capture at low light levels, so it is less invasive than the use of flash exposure, which is painful. As such, the capture of continuous illumination low light level images is expected to remove a major barrier to universal screening and to promote the practice of routine retinal monitoring. However, in other embodiments the invention may be practiced with other image capture technology, such as the direct digital output DCS-420 Kodak single frame camera. Such a camera may provide higher resolution, although it would generally require an auxiliary flash source to produce its larger format images.

As noted above, in the field of retinal evaluation, a principal application of the images will be the acquisition of high resolution true color baseline images, including stereo pair images, of the retina and retinal vasculature, and the acquisition of stereographic motion pictures of standardized ophthalmologic procedures such as fluorescein angiography, which will reveal the dynamic properties of circulation at time the test is run. True color images at the described twenty micron or better level of resolution will provide sufficient information for a trained ophthalmologist to evaluate the status of retinal pathology or incipient pathological conditions, to evaluate the efficacy of medications, and provide prognostic consultations. While the video data is acquired and is viewed at two different sites in real time, the described teleconferencing and network communications links between the two sites allow the ophthalmologist to discuss the patient's condition and details of the exact images as the procedure is being effected, and to adjust the imaging parameters or arrange for further views as appropriate. In addition, the storage of video frame data and the video monitor 30a at the image acquisition site allow the referring physician or treating technician to show the patient the precise images involved and discuss the implications of what is seen on the screen. Applicants have found that such direct sharing of medical information, enabling the patient to see the actual images and discuss the microscopic changes involved, strongly impresses the individual with the concrete reality of his medical condition, bolstering the importance or relevance of his own health and its interrelationship with lifestyle and behavioral activities. Thus, this manner of establishing a treatment relation with the patient is less alienating, and encourages the patient to make a commitment to continue proper treatment.

At the image examination station, the display monitors are preferably true color twenty-one inch or larger monitors, or where group consultations or teaching are to use the images, a stereo-capable projector with low-persistence green phosphor is used to allow projection of sequences of retinal images.

The overall image management program is preferably implemented by adding it to a medical records platform that links patient records to the image records, and allows both to be augmented or annotated at the examination stations. The images are preferably acquired and marked as sets of seven standard fields as shown in FIG. 2A and defined in the Early Treatment Diabetic Retinopathy Study (ETDRS). The image display software provides a first display mode in which the seven fields are displayed as thumbnail stereo pair images, as shown in FIG. 2B, with the same layout used for both left and right eyes. The workstation image management software allows the operator to select the type of fall-scale image display so that by clicking on the left one of a thumbnail stereo image, the actual full-scale image or chosen set of images is displayed. Display modes are provided for viewing individual fields, as stereograms, or pairs of the fields for comparison, as well as pairs such as present image/previous visit, filtered or color-enhanced images, and grid-matched magnified images to better exhibit particular tissue.

In general, the image display sequences provide all the diagnostic features required by the ophthalmologist to make an assessment of the level of diabetic retinopathy. The design preferably provides a screen without window decorations maximizing available display area and image viewing without the distractions of display icons or pull down menus. The display functions incorporate true color stereo display, with as many as four separate retinal images displayed in stereo on the same screen. This provides the facility for meaningful comparative evaluations. For example image fields from three prior visits can be displayed with a corresponding image field from the current visit to determine rate of progression of retinopathy. Another feature provides for the side-by-side display of ETDRS standard retinal images previously scanned into the system, to be compared with the patient retinal images so as to facilitate accurate level of retinopathy determination. This provides a standard for assessment of level of retinopathy, namely a comparison with the ETDRS standard retinal images. In addition to the color images the image management software allows display of images in the traditional red-free format which provides an enhanced contrast of the retinal vasculature. In this case, the software simply applies a digital filter to the already acquired retinal images in order to provide an image comparable to a red-free image. That is, the software sets the red and blue color components of the image equal to zero, to automatically display a green high contrast image of the retinal vasculature. The flexibility inherent in these digitized images for color manipulation provides enhanced diagnostic information from different layers of the retina. For example, blue light is primarily reflected from the front regions of the retina while red light is primarily reflected from deeper retina regions. Thus by appropriate color manipulation, the processed images selectively provide pathological information from different depths of the retina. Significantly, these images may be achieved from a single video image, without using filtered sources or other special preparations at the image acquisition stage.

As noted above, by simple zeroing of the red and blue components of an image, a high contrast green image is obtained. The invention further contemplates a modified fluorescein angiograph procedure, wherein monochrome fluorescein angiograms are captured as moving pictures, i.e., as a sequence of successive stereo flames. For such imaging applicant has modified the back of a Donaldson fundus camera, with two DEI-470 Optronic cameras coupled to the retinal focal planes. The cameras interface with a pair of J-300 sound and motion video image capture cards to acquire a fast image sequence. For this imaging, a fiber bundle is interfaced to the camera to supplement the viewing illumination. With this arrangement, it is possible to avoid reliance on flash exposure as required in the prior art, and to employ light levels comparable to viewing levels.

Images may also be acquired by the aforesaid Optronics camera fitted to an indirect ophthalmoscope. Focusing may be by set up to respond to a foot switch or voice activated control. The camera may be interfaced to one of the viewing eyepieces of the slit lamp. This instrumentation provides good quality anterior segment images, with lesser viewing light intensity than is applied by the slit lamp.

In addition to the communication of images and medical information between persons involved in the procedure, the network may carry data signals including control or image adjustment signals by which the ophthalmologist at the examination unit 20 directly controls the image acquisition occurring at the acquisition unit 12. In particular, such command signals as zoom magnification, steering adjustments, and wavelength of field illumination may be selectively varied remotely to achieve desired imaging effect. Thus, questionable tissue structures requiring greater magnification or a different perspective for their elucidation may be quickly resolved without ambiguity by varying such control parameters. Furthermore, by switching illumination wavelengths views may be selectively taken to represent different layers of tissue, or to accentuate imaging of the vasculature and blood flow characteristics. In addition, where a specialized study such as fluorescence imaging is undertaken, the control signals may include time varying signals to initiate stimulation with certain wavelengths of light, to initiate imaging at certain times after stimulation or delivery of dye or drugs, or other such precisely controlled imaging protocols. The digital data signals for these operations may be interfaced to the ophthalmic equipment in a relatively straightforward fashion, provided such equipment already has initiating switches or internal digital circuitry for controlling the particular parameters involved, or is capable of readily adapting electric controls to such control parameters as system focus, illumination and the like.

For implementation of a prototype embodiment, a UNIX operating system of Digital Equipment Corporation was employed with a separate program X/II R5 to control the graphics display. This allowed for images to be displayed without window decorations, increasing the available image area on the screen and simplifying the projection of stereo images. The electronic medical record hardware required only a processor such as an Intel 486, with 8MB of memory and a 300 MB disk drive, a keyboard, and a pen pad display/entry system. The pen pad/display is installed such that it appears in the same plane as the image monitor for the image acquisition. The necessary software on a windows based work group system includes standard programs for pen pad operation, the Clinictec NextGen medical record platform, and an oracle driver for accessing the server in a relational database.

In a like manner, certain procedures, such as laser photocoagulation of retinal vessels, for which the necessary ophthalmic instrumentation already involves highly integrated and computer controlled aiming, focusing and actuation circuitry, may be adapted to remote operation in conjunction with the stereo imaging work stations provided by the present invention. In these instances, the ophthalmologist at examination station 20 may not only view the stereo images and identify pathologic sites or processes, but may actively control the photocoagulation unit in real time as the procedure continues. It will be understood that the imaging and ophthalmic treatment instrumentation in this case will generally include a steering and stabilization system which maintains both instruments in alignment and stabilized on the structures appearing in the field of view. However, in view of the small but non-negligible time delays still involved between image acquisition and initiation of diagnostic or treatment activity at the examination site 20, in this aspect of the invention, the invention contemplates that the system control further includes image identification and correlation software which allows the ophthalmologist at site 20 to identify particular positions in the retinal field of view, such as pinpointing particular vessels or tissue structures, and the image acquisition computer 30 includes image recognition software which enables it to identify patterns in the video frames and correlate the identified position with each image frame as it is acquired at the acquisition site 12. For example, the image recognition software may lock onto a pattern of retinal vessels. Thus, despite the presence of saccades and other abrupt eye movements of the small retinal field which may occur over relatively brief time intervals, the ophthalmic instrumentation is aimed at the identified site in the field of view and remote treatment is achieved.

In addition to the foregoing operation, the invention further contemplates that the images provided by acquisition unit 12 are processed for photogrammetric analysis of tissue features and blood flow characteristics. This is accomplished as follows. An image acquired by unit 12 is sent to an examination unit, illustratively unit 20*b*, where it is displayed on the screen. As indicated schematically in the figure, such image may include a network of blood vessels having various diameters and lengths. These vessels include both arterial and venous capillaries constituting the blood supply and return network. The features of these vessels (e.g., spectral reflectance) clearly indicate which network is which, and the relative sizes of each vessel and their branch connection are also clearly visible. At the examination unit 20*b*, the workstation is equipped with a photogrammetric measurement program which enables the technician to place a cursor on an imaged vessel, and moving the cursor along the vessel while clicking, have the software automatically determine the width of the vessel and the subvessels to which it is connected, as well as the coordinates thereof.

The software for noting coordinates from the pixel positions and linking displayed features in a record, as well as submodules which determine vessel capacities and the like, are straightforward and readily built up from photogrammetric program techniques. Work station protocols may also be implemented to automatically map the vasculature, or to compare two images taken at historically different times and identify or annotate the changes which have occurred, highlighting for the operator features such as vessel erosion, tissue which has changed color, or other differences. In addition, a user graphical interface allows the specialist to type in diagnostic indications linked to the image, or to a particular feature appearing at a location in the image, so that the image or processed version of it becomes more useful.

With suitable training, the relative health of the vessel, its blood carrying capacity and the like may also be visually observed and noted. This photogrammetric analysis allows a road map of the vasculature and its capacity to be compiled, together with annotations as to the extent of tissue health or disease apparent upon such inspection. Thus, a very precise and well-annotated medical record may be readily compiled and may be compared to a previously taken view for detailed evidence of changes over a period of time, or may be compared, for example, to immediately preceding angiographic views in order to assess the actual degree of blood flow occurring therein. As with the ophthalmologist's note pad entries at examination unit 20*a*, the measurement entries at examination unit 20*b* become an annotated image record and are stored in the central library as part of the patient's record.

In addition to the foregoing, it is understood that for the stereographic video images the computer processors include three-dimensional imaging software which operates on the pairs of image frames sent from the acquisition site 12 to compose detail images and enhanced side views, i.e., to perform computerized rendering with a perspective not formerly possible in ophthalmic imaging, which are derived from accentuating color differences in corresponding points of adjacent image frames to show the curvature, shading, color and other visible features of the microscopic structures appearing in the video frames. Thus, for example, while the fundus camera takes a series of views across a baseline which is limited by the width of the dilated pupil and is essentially an almost vertical perspective view, the video software may combine points from different color planes to compose an enhanced perspective view of a retinal vessel where it attaches to or rises out of underlying tissue, and these features which provide strong diagnostic information and were previously visible only in blurry or vague sectional views, may be represented as processed video lateral or perspective side views of the relevant tissue or fascia in which their physical structure is clearly visible. Various artifacts of specular or diffuse reflection may be eliminated based on color or on light intensity limits, and contrast may be readily adjusted by offset or regional image transformations to reveal new diagnostic indications. These artificially generated images may be composed in real time as requested by the technician or ophthalmologist in the examination room, or derived later, and may also be annotated as described above and saved as critical parts of the record. Thus, the system of the present invention allows the remote stereographic imaging of retinal tissue, the manipulation and formation of new images, and the immediate linking and annotation of diagnostic data into hybrid image/text records for storage in the medical records system, as well as remote control of imaging or treatment instruments.

The various prototype embodiments discussed above-Donaldson camera, slit lamp, indirect ophthalmoscope and other instruments illustrate a range of ophthalmic imaging instruments to which applicants imaging invention and medical/image record management and recording system apply. Unlike a simple medical record system, the present invention changes the dynamics of patient access to care, and the efficiency of delivery of ophthalmic expertise in a manner that solves an enormous current health care dilemma, namely, the obstacle to proper universal screening for diabetic retinopathy. A basic embodiment of the invention being thus disclosed and described, further variations and modifications will occur to those skilled in the art, and all such variations and modifications are encompassed within the scope of the invention as defined in the claims appended hereto.

What is claimed is:

1. A system for examining the retina of an eye, comprising
   an image acquisition unit including an ophthalmic viewing instrument and an electronic imaging camera coupled to said instrument for generating true color digital stereoscopic video image frames representative of a retina of an eye,
   a computer network interfaced to said image acquisition unit for sending and receiving said stereoscopic video image frames, said computer network including storage for storing said stereoscopic video image frames, and
   a display coupled to said computer network for displaying said stereoscopic video image frames for examination.

2. A system according to claim 1 wherein said image acquisition unit further includes an electronic image display at said viewing instrument and an adjustable lamp source for matching said true color digital image frames to visual images viewed through said instrument.

3. A system according to claim 2 wherein said stereoscopic video image frames generated by said image acquisition unit are high resolution images.

4. A system according to claim 2 wherein said electronic imaging camera generates video image signals forming a sequence of time-successive images.

5. A system according to claim 1 wherein said computer network organizes and displays on said display, plural high resolution retinal images in an array for comparison of said retinal images.

6. A system according to claim 1 wherein said image acquisition unit includes means for generating frames of retinal image data separated by a base, and said display includes means for displaying stereo true color images formed of said frames.

7. A system according to claim 1 wherein said computer network includes
   a monitor for displaying true color high resolution images,
   a medical records platform for accessing and storing medical records, and
   a graphic interface for allowing a user to identify and select diagnostic features appearing in the images displayed on the monitor and to store the images and identified features as medical records in a relational database.

8. A system according to claim 7, wherein said computer network is located at a hub location having a plurality of said monitors set up as workstations such that trained technicians view, identify, and select features in images from image acquisition means located at a plurality of different sites to identify retinopathy, thereby providing image-based remote expert screening.

9. A system according to claim 1 wherein said computer network includes a relational database for organizing said true color digital signal frames and for accessing image and text data together as a medical record, said computer network including a graphic interface for processing color-enhanced images from the image data in a record.

10. A system according to claim 1 further comprising an image database memory coupled to said computer network for storing one or more data records, each including an image field for storing one of said image frames and an identification field for storing diagnostic text identification associated with features in the stored image frame of said data record.

11. A system according to claim 1 wherein said image acquisition unit operates to image with continuous non-flash illumination at light levels below 5 lux.

12. A system according to claim 1 wherein the image examination unit is adapted to remotely control said image acquisition unit to selectively generate said image signals.

13. A system according to claim 1 further comprising an ophthalmic treatment instrument coordinated with said image acquisition unit for delivering treatment to said retina as it is imaged.

14. A system according to claim 13 wherein said network interconnects a controller at said display remote from said image acquisition unit to control said ophthalmic treatment instrument while an operator views the display.

15. A system according to claim 1, wherein said computer network interfaces with said storage and display to create image/text records such that a patient's medical record may be stored at a work station in digital form and accessed for display and evaluation.

16. A system for retinal imaging comprising
    an image acquisition unit including an ophthalmic viewing instrument and an electronic imaging camera for capturing true color digital images through said instrument
    a continuous light source which is adjustable to vary color of the digital images,
    an image processor for controlling said continuous light source; and
    a computer network, connected to said image processor, for storing the true color digital images taken by said camera.

17. A system according to claim 16, further comprising an examination system connected to said network, the examination system comprising means for accessing said images and medical records, and means for displaying said images adjacent to one another for examination.

18. A system according to claim 16, further comprising digital color filter means for applying a digital color filter to said true color images to form high contrast images.

19. A system for examining the retina of an eye, comprising:

an image acquisition unit including an ophthalmic viewing instrument and an electronic imaging camera coupled to said instrument for generating true color digital image signal frames representative of a retina of an eye, an image examination unit, located remotely from said image acquisition unit, said image examination unit generating control signals for controlling said image acquisition unit, and a computer network interfaced to said image acquisition unit and image examination unit for sending and receiving said image signal frames from said image acquisition unit and for transmitting said image signal frames to said image examination unit, said computer network including storage within which said image frames are stored.

20. A system according to claim 19 wherein the image examination unit is adapted to remotely control said image acquisition unit to selectively generate said image signals.

21. A system according to claim 19 further comprising an ophthalmic treatment instrument coordinated with said image acquisition unit for delivering treatment to said retina as it is imaged.

22. A system according to claim 21 wherein said network interconnects a controller at said display remote from said image acquisition unit to control said ophthalmic treatment instrument while an operator views the display.

23. A system according to claim 22 wherein said network interconnects a controller at said display remote from said image acquisition unit to control said ophthalmic treatment instrument while an operator views the display.

24. A system according to claim 20 wherein said telecommunications link is a fiber optic link for conveying images of the retina.

* * * * *